(12) United States Patent
Hoctor et al.

(10) Patent No.: US 7,925,068 B2
(45) Date of Patent: Apr. 12, 2011

(54) METHOD AND APPARATUS FOR FORMING A GUIDE IMAGE FOR AN ULTRASOUND IMAGE SCANNER

(75) Inventors: Ralph Thomas Hoctor, Saratoga Springs, NY (US); Mirsaid Seyed Bolorforosh, Guilderland, NY (US)

(73) Assignee: General Electric Company, Niskayuna, NY (US)

(*) Notice: Subject to any disclaimer, the term of this patent is extended or adjusted under 35 U.S.C. 154(b) by 1044 days.

(21) Appl. No.: 11/670,286

(22) Filed: Feb. 1, 2007

(65) Prior Publication Data

US 2008/0187193 A1   Aug. 7, 2008

(51) Int. Cl.
| | |
|---|---|
| G06K 9/00 | (2006.01) |
| G06K 9/03 | (2006.01) |
| A61B 5/05 | (2006.01) |
| G06F 3/033 | (2006.01) |
| G09G 5/00 | (2006.01) |

(52) U.S. Cl. ........ 382/132; 382/309; 382/128; 600/424; 345/158; 345/629; 345/630

(58) Field of Classification Search .......... 382/128, 382/132, 158, 309; 345/158, 629, 630; 600/424, 600/437

See application file for complete search history.

(56) References Cited

U.S. PATENT DOCUMENTS

| | | | | |
|---|---|---|---|---|
| 3,751,976 A | * | 8/1973 | Pike | 73/614 |
| 4,182,173 A | * | 1/1980 | Papadofrangakis et al. | 73/861.27 |
| 4,197,751 A | * | 4/1980 | Vilkomerson et al. | 73/633 |
| 4,553,437 A | * | 11/1985 | Luthra et al. | 73/602 |
| 4,631,965 A | * | 12/1986 | De Vadder et al. | 73/602 |
| 5,109,857 A | * | 5/1992 | Roundhill et al. | 600/437 |
| 5,176,141 A | * | 1/1993 | Bom et al. | 600/467 |
| 5,178,151 A | * | 1/1993 | Sackner | 600/485 |
| 5,787,889 A | * | 8/1998 | Edwards et al. | 600/443 |
| 5,846,204 A | * | 12/1998 | Solomon | 600/463 |
| 5,891,039 A | * | 4/1999 | Bonnefous et al. | 600/454 |
| 6,012,458 A | * | 1/2000 | Mo et al. | 600/437 |
| 6,106,470 A | * | 8/2000 | Geiser et al. | 600/443 |
| 6,108,439 A | * | 8/2000 | Ishiguro | 382/131 |
| 6,117,081 A | * | 9/2000 | Jago et al. | 600/443 |
| 6,169,817 B1 | * | 1/2001 | Parker et al. | 382/131 |

(Continued)

FOREIGN PATENT DOCUMENTS

WO   WO 0205217   *   7/2000

OTHER PUBLICATIONS

Hwang et al. "A Potetial Field Approach to Path Planning" IEEE Transactions on Robotics and Automation, vol. 8, No. 1, Feb 1992, pp. 23-32.*

(Continued)

*Primary Examiner* — Bhavesh M Mehta
*Assistant Examiner* — Mia M Thomas
(74) *Attorney, Agent, or Firm* — Scott J. Asmus (57) ABSTRACT

A method for producing a three-dimensional guide image of an object to be scanned during an ultrasound scan. The method comprises insonifying the object, receiving return echoes from the object, processing the return echoes to generate a data set representing the object, comparing the data set with a plurality of shape models, selecting a best fit shape model responsive to the step of comparing and displaying the best fit shape model as the guide image.

28 Claims, 2 Drawing Sheets

U.S. PATENT DOCUMENTS

| | | | |
|---|---|---|---|
| 6,216,027 B1* | 4/2001 | Willis et al. | 600/424 |
| 6,263,093 B1* | 7/2001 | Mochizuki | 382/128 |
| 6,283,917 B1* | 9/2001 | Jago et al. | 600/437 |
| 6,295,464 B1* | 9/2001 | Metaxas | 600/407 |
| 6,309,356 B1* | 10/2001 | Ustuner et al. | 600/443 |
| 6,332,089 B1* | 12/2001 | Acker et al. | 600/424 |
| 6,422,723 B1* | 7/2002 | Walters | 362/471 |
| 6,425,869 B1* | 7/2002 | Rafter et al. | 600/458 |
| 6,464,638 B1* | 10/2002 | Adams et al. | 600/443 |
| 6,468,218 B1* | 10/2002 | Chen et al. | 600/443 |
| 6,527,718 B1* | 3/2003 | Connor et al. | 600/439 |
| 6,556,695 B1* | 4/2003 | Packer et al. | 382/128 |
| 6,701,174 B1* | 3/2004 | Krause et al. | 600/407 |
| 6,726,630 B2* | 4/2004 | Kawagishi | 600/458 |
| 6,751,492 B2* | 6/2004 | Ben-Haim | 600/374 |
| 6,773,402 B2* | 8/2004 | Govari et al. | 600/459 |
| 6,802,219 B2* | 10/2004 | Joseph et al. | 73/290 R |
| 6,950,689 B1* | 9/2005 | Willis et al. | 600/407 |
| 7,236,618 B1* | 6/2007 | Chui et al. | 382/128 |
| 7,299,806 B2* | 11/2007 | Lokhandwalla et al. | 600/445 |
| 7,371,219 B2* | 5/2008 | Sakaguchi et al. | 600/455 |
| 7,399,278 B1* | 7/2008 | Ross | 600/437 |
| 7,517,318 B2* | 4/2009 | Altmann et al. | 600/459 |
| 7,601,121 B2* | 10/2009 | Pagoulatos et al. | 600/443 |
| 7,604,601 B2* | 10/2009 | Altmann et al. | 600/463 |
| 7,697,972 B2* | 4/2010 | Verard et al. | 600/424 |
| 7,740,584 B2* | 6/2010 | Donaldson et al. | 600/443 |
| 7,831,076 B2* | 11/2010 | Altmann et al. | 382/128 |
| 7,835,785 B2* | 11/2010 | Scully et al. | 600/424 |
| 2003/0092992 A1* | 5/2003 | Kawagishi | 600/458 |
| 2004/0044283 A1* | 3/2004 | Yoneyama | 600/437 |
| 2004/0059217 A1* | 3/2004 | Kessman et al. | 600/424 |
| 2004/0068178 A1* | 4/2004 | Govari | 600/424 |
| 2004/0093940 A1* | 5/2004 | Joseph et al. | 73/290 V |
| 2004/0147920 A1* | 7/2004 | Keidar | 606/34 |
| 2004/0249287 A1* | 12/2004 | Kawashima et al. | 600/462 |
| 2005/0004462 A1* | 1/2005 | Sakaguchi et al. | 600/441 |
| 2005/0093847 A1* | 5/2005 | Altkorn et al. | 345/184 |
| 2005/0113684 A1* | 5/2005 | Lokhandwalla et al. | 600/427 |
| 2005/0124886 A1* | 6/2005 | O'Donnell et al. | 600/443 |
| 2005/0131295 A1* | 6/2005 | Li | 600/443 |
| 2006/0247530 A1* | 11/2006 | Hardin et al. | 600/466 |
| 2007/0014446 A1* | 1/2007 | Sumanaweera et al. | 382/128 |
| 2007/0276237 A1* | 11/2007 | Li | 600/437 |
| 2007/0276247 A1* | 11/2007 | Chalana et al. | 600/447 |
| 2008/0194957 A1* | 8/2008 | Hoctor et al. | 600/443 |
| 2009/0036775 A1* | 2/2009 | Ikuma et al. | 600/443 |
| 2010/0030079 A1* | 2/2010 | Hamada | 600/443 |
| 2010/0228118 A1* | 9/2010 | Maschke | 600/424 |

OTHER PUBLICATIONS

Ballester et al. "Surgical planning and simulation based on virtual physiclogical models" ALMA IT systems, Barcelona, Spain. pp. 1-6 (2009).*

Dudkin et al. "Digital Processing of Images in Physiological Studies" Neuroscience and Behavioral Physiology, vol. 29, No. 2, 1999, pp. 1-5.*

Jin et al. "Characterization of One Dimensional Capacitive Micromachined US Immersion Transducer Arrays" IEEE Transactions on US, Ferroelectrics, and Freq. Control, vol. 48. No. 3, May 2001 pp. 1-11.*

Goldberg et al. "Multilayer Piezoeletric Ceramics for Two-Dimensional Array Transducers" IEEE Transactions on US, Ferroelectrics, and Frequency Control, vol. 41, No. 5, Sep. 1994, pp. 1-11.*

* cited by examiner

METHOD AND APPARATUS FOR FORMING A GUIDE IMAGE FOR AN ULTRASOUND IMAGE SCANNER

FIELD OF THE INVENTIONS

This invention relates generally to ultrasound imaging and in particular to an apparatus and method for producing a guide image to assist the user in acquiring a desired image during an ultrasound imaging process.

BACKGROUND OF THE INVENTIONS

A conventional ultrasound imaging system includes an array of ultrasonic transducers that transmit an ultrasound wave (a transient pressure wave) during a transmit mode and receive a reflected wave reflected from an object under study during a receive mode. The spatial response to this ultrasound wave is referred to as an ultrasound beam. In general, the overall (two-way) beam is a combination of two separate beams: a transmit beam, which represents the degree to which energy is deposited in the object, and a receive beam, which represents a system response to echoes originating at various points in space. The signals generated by the transducers responsive to the received pressure wave are processed and the results displayed as a visual image of the object.

The array typically includes a multiplicity of transducers configured as a linear array or row, each transducer driven by a separate signal voltage during the transmit mode. Selecting a time delay (relative to a reference time) for the signal voltage applied to each transducer controls a direction of the ultrasonic beam energy transmitted by the individual transducers. In addition, controlling the amplitude of the signal voltage applied to each transducer can be used to lower energy present in sidelobes of the ultrasound beam.

Controlling the time delay steers the ultrasonic energy emitted by the transducers to produce a net ultrasonic wave that travels along (scans) the object in a desired direction or along a scan line (also referred to as an A-line), with the energy focused at a selected point on the scan line. That is, the transmit energy is focused or concentrated at a fixed range (fixed focal point) from the transducer array, maximally localizing the energy at that range. At other ranges (distances from the transducer array) the energy is localized to a lesser extent, producing a broader beam. Thus although the energy is focused at only a single point on the scan line, the energy at proximate points (the points comprising a focal zone) may be sufficient to produce a reflected beam that can be processed to render an image with sufficient lateral resolution.

Similar beam-combining principles are employed when the transducers receive the reflected ultrasonic energy from the scan line. The voltages produced at the receiving transducers are controllably delayed and summed so that the net received signal response is primarily representative of the ultrasonic energy reflected from a single focal zone along the scan line of the object.

To generate a two dimensional or planar image of the object (and recognizing that ultrasound imaging occurs in the near field), during the receive mode the transducers are dynamically focused at successive ranges from the transducer array (depths into the object being scanned) along the scan line as the reflected ultrasonic waves are received. The focused range is based on the round-trip travel time of the ultrasound pulse. Controlling the time-delay associated with each transducer focuses the received energy at the desired time-variant range or depth. Such dynamic focusing in the receive mode produces a usable response at the focal point and a range of distances near the focal point. The range over which the two-way response of the system is well-focused is referred to as the depth of field. Outside the depth of field the image quality suffers and the reflections are not usable to produce the image.

As can be appreciated, the instantaneous beam steering and signal combining capabilities of the linear transducer array are capable of producing only a 2D image of the object, where the image is in the plane normal to the array surface and contains the centers of the array elements.

Figure 1:
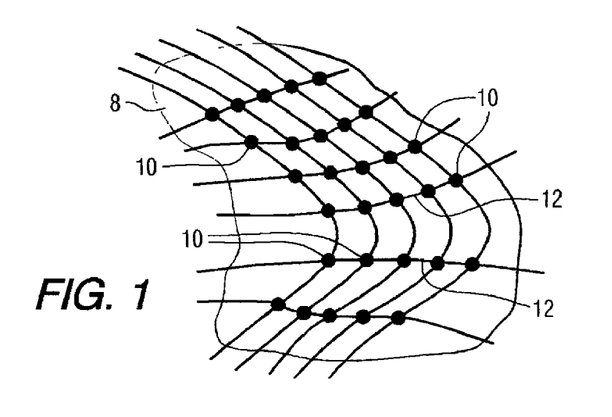
FIG. 1 illustrates a portion of a surface of a deformable model according to the prior art.

Deformable models are known in the art and were first used in computer animation to produce realistic motion of an elastic object. A deformable model models elastic object surfaces using connected mass elements according to various physics-based or geometric techniques. As illustrated in FIG. 1, an object surface 8 is modeled as grids of point masses 10. Each mass is connected to one or more adjacent masses by a rigid elastic rod 12 that exerts a return force on the connected masses when bent, stretched or compressed away from its rest state. Different masses can also be connected by other exemplary connecting rods.

The dynamics of the surface 8 can be defined at each mass by a force balance equation such as:

$$\underbrace{m\ddot{x} + k\dot{x}}_{\text{forces from object dynamics}} + \underbrace{\delta E(x)}_{\substack{\text{internal} \\ \text{force}}} = \underbrace{f_{user}}_{\substack{\text{external} \\ \text{force}}}$$

where x is a position vector of the masses, m is the mass of each point or particle, k is a viscous friction constant (often assumed to be zero) and the variational symbol $\delta E(x)$ is a restoring force proportional to the local curvature of the surface at the location of the point mass. The dots represent vector component-wise time derivatives. The variable x and the x-dot variables are vectors in a three dimensional space that describe the instantaneous condition (location, velocity, acceleration, etc.) of the model at any instant in time. State equations defining the deformable model are derived from the force balance equation and consist of state variables and their derivatives.

The force balance equation depicts the balance of forces resulting from motion of the point masses (forces based on the object dynamics), restoring forces arising from the curvature of the surface at the location of the point mass and external forces controlling motion of the modeled object. For the computer animation application, external forces are specified by the animator.

For medical image analysis, the external forces are represented by a potential field that is derived from the acoustic echoes that form the image. Strong image echoes form a strong potential field and weak image echoes (dark regions of the image) form a weak potential field. The echo magnitude and the potential field derived from it can be regarded as a type of charge attracting oppositely charged point masses of the object. The model masses are therefore attracted to the strong potential field regions, causing the model to conform to the image. The model masses are only weakly attracted to the weak potential field derived form the weak image echoes.

When a deformable model is used for static segmentation of a still image in the prior art, the external forces responsive to the potential field are generally more important than the dynamics of the model's surface. Application of the deformable model to the static segmentation application requires only that the model's final configuration represent an equilibrium position of the surface in the external potential field generated by the image. The model's transient response can be any response that is convenient to the model designer. The fastest static model response occurs when the model points have very low mass, minimizing the effects of object dynamics. (This type of response also eliminates overshoot and the resulting oscillations that can occur in linear systems. Such oscillations tend to slow the model's response to the potential field.)

In effect, the deformable model, absent consideration of the object's dynamics, is a method for managing a constrained optimal fit of the model to the image. The constraint is a smoothness constraint and is represented by the elastic return forces of the model. The objective function is a measure of the fit of the model to the image and is represented by the potential energy field as derived from the image. This technique can also be applied to tracking a moving surface using a sequence of complete images, since every image can be fit separately using constraints derived from images taken at about the same time to ensure a smooth evolution of the model shape through the image sequence.

The model set forth in the equation above allows the state variables (e.g., acceleration, velocity and position of the masses) to evolve in response to the various forces that act on them. This evolution is simulated by a discrete-time computational process in which the continuous-time state transition matrix associated with the equations of motion above is integrated to form a discrete time system matrix. Each time a multiplication of the state vector by this matrix is performed, new external force information can be incorporated into the computation as a discrete time driving function. The details of such discrete time systems are well known. For example, consult Digital Control of Dynamic Systems, by G. F. Franklin and J. D. Powell (Addison Wesley, 1980).

BRIEF SUMMARY OF THE INVENTION

One embodiment of the invention comprises a method for producing a three-dimensional guide image of an object to be scanned during an ultrasound scan, comprising: insonifying the object, receiving return echoes from the object, processing the return echoes to generate a data set representing the object, comparing the data set with a plurality of shape models, selecting a best fit shape model responsive to the step of comparing and displaying the best fit shape model as the guide image.

Another embodiment of the invention comprises an ultrasonic imaging apparatus for producing a three-dimensional guide image of an object. The apparatus comprises a plurality of ultrasonic transducers for generating ultrasonic energy during a first scan, for receiving first echoes from the object and for generating first signals responsive to the first echoes, a processor for generating a data set according to the first signals, the data set representing the object, the processor for selecting a best fit shape model from among a plurality of shape models responsive to the data set and a first display for displaying the best fit shape model as the guide image.

BRIEF DESCRIPTION OF THE DRAWINGS

The present invention can be more easily understood and the advantages and uses thereof more readily apparent when the following detailed description of the present invention is read in conjunction with the figures wherein.

In accordance with common practice, the various described features are not drawn to scale, but are drawn to emphasize specific features relevant to the inventions. Like reference characters denote like elements throughout the figures and text.

DETAILED DESCRIPTION OF THE INVENTIONS

Before describing in detail the particular method and apparatus related to producing a guide image for use during ultrasound imaging, it should be observed that the present invention resides primarily in a novel and non-obvious combination of elements and process steps. So as not to obscure the disclosure with details that will be readily apparent to those skilled in the art, certain conventional elements and steps have been presented with lesser detail, while the drawings and the specification describe in greater detail other elements and steps pertinent to understanding the inventions.

The presented embodiments are not intended to define limits as to the structures, elements or methods of the inventions, but only to provide exemplary constructions. The embodiments are permissive rather than mandatory and illustrative rather than exhaustive.

As ultrasound scanners become less expensive they will be used in more applications and by less experienced users. Performing the scan is significantly facilitated and better results are achieved if the operator can visualize a 3D map of the relevant anatomical object (source object) and its surrounding objects. Experienced scanner operators can typically mentally visualize the source object or source volume, but such visualization can be problematic for novice users, possibly resulting in poor quality images or images that omit important anatomical features of the source volume.

To promote wider use of the scanners, especially among operators who lack detailed training and who may not be able to visualize the source volume, it is desired to present the operator with a guide to the insonified region during the scanning process. Specifically, a technical effect of one embodiment of the present invention displays a 3D guide image or map of the source volume and during the imaging process displays the current scan plane on the 3D map, allowing the user to visualize the current scan plane relative to the region to be insonified.

In one embodiment, the 3D map or guide image includes labels indicating the location of important anatomical features within the imaged volume. The labels are intended to assist the operator during the scanning process and ensure that the desired features are imaged. Preferably, the inventions find applications to imaging abdominal organs or to other imaging scenarios where the source volume is not in constant motion, as it may not be possible to provide an acceptable 3D guide image of a moving source volume, such as the heart.

In one embodiment the displayed 3D guide image or map comprises a relatively low-resolution, semi-transparent, smooth rendering. The current scan plane is superimposed on the image, allowing the operator to control motion of the transducer probe to ensure the desired source volume regions are insonified during the scan process.

To form the guide image, the operator sweeps the image plane through the sample volume (free hand) by manually moving the transducer probe (e.g., transducer array) in a sweeping motion at a constant speed. Each image scan acquired during this manual sweep produces a cross-sectional cut or plane through the source volume (e.g., a bodily organ). By moving the probe at a constant speed (to the extent practical) the operator ensures that the individual image planes are parallel. Note that during a normal ultrasound diagnostic scan the operator typically changes the probe speed to capture desired images and may twist the probe. Such a probe twist produces an image plane that intersects, at an angle determined by the amount of the twist, one or more of the parallel planes captured by the constant sweep motion. The acoustic responses from the image plane free hand sweep are processed, as described below, to produce a 3D data set representing the free hand scanned source volume.

In one embodiment a 3D data set representing the free hand scanned source volume is created by processing the return echoes using a speckle correlation approach. It is known that the return echoes from the scattering volume (the insonified region of the source object), generated responsive to the coherent reception of the transmitted acoustic wave, present a pattern of time invariant constructive and destructive interference regions referred to as a speckle pattern. The return echoes from the scattering volume are correlated as a function of the location of the echo site, since they represent the characteristic interaction of the scattering volume with the transmitted acoustic energy.

As the image plane moves (i.e., the operator sweeps the transducer array probe) a new speckle pattern is produced and regions of the new speckle pattern are correlated with corresponding regions of prior speckle patterns. This continuing correlation process tracks the image plane through space to associate successive image planes. By correlating similar regions in pairs of 2D image planes, the angle and displacement between two scan planes can be determined. The correlation process thereby registers the sequence of 2D scanned image planes into a data set (i.e., a 3D data set) representing the free hand scanned volume. The registered data set so produced will not, in general, be sampled in a uniform manner in space, and can be interpolated onto a regular sampling grid for further processing.

The 3D data set is converted to a free hand scan model, for example a "low mass" deformable model, that depicts the size and shape of the free hand scanned source volume. One technique for creating the model from the data set comprises generating a potential field, as described above, responsive to the 3D data set. The potential field then acts on a model surface to conform the model surface to the potential field and thus to the tissue interfaces present in the 3D data set. In one embodiment the process of fitting the free hand scan model to the data set further comprises morphological filtering or another smoothing process to reduce the effect of speckle in the 3D data set. As known by those skilled in the art, other models and modeling techniques can be used to transform the 3D data set into a model that properly captures the size, shape and orientation of the free hand scanned volume.

To identify the source volume (e.g., bodily organ) represented by the free hand scan model, a library of candidate static shape models is provided. These static models comprise points joined by connecting segments. Each model has a fixed shape and is relatively finely sampled over its surface to ensure accurate identification of the shape model that has the best fit with the free hand scan model. Each shape model also includes an identification of the important anatomical features of the associated organ that can be displayed with the guide image.

The free hand scan model is compared with the candidate shape models to determine the model having the highest correlation. The highest correlation model is selected and serves as the guide image.

According to one embodiment, the comparison process comprises determining the shape model that generates a minimum potential energy difference with the free hand scan model. That is, each shape model in the library (data base) generates a potential field that acts on the free hand scan model. The potential field generating the fewest modifications to the free hand scan model is the best-fit shape model.

According to one embodiment the scale of the free hand scan model is modified to create scaled versions thereof and each resulting scaled version is compared with the library of candidate shape models to find the best fit model. Alternatively, in another embodiment the free hand scan model size is fixed and the library of shape models includes different scales (sizes) for each model.

According to yet another embodiment, multiple shape models each having a different rotation, are included in the library. This embodiment in particular compensates for angular rotation of the free hand scan model due to angular displacement of the transducer probe during the free hand scan. However, because the range of angles from which the source volume may be insonified during the freehand scan is limited, only a correspondingly limited number of source volume rotations should be included for each shape model.

In some cases, the shape and size of a library model are correlated, a feature that can be incorporated into the correlation process. For example, a scanned source volume that appears to be a very large kidney may actually be a medially-placed single kidney, which is a known birth defect. Such a kidney is more elongated than a normal kidney, and therefore requires a unique library model. But in those situations where the size and shape of the model are correlated, it may not be necessary to compare both the model shape and the model size with the free hand scan. It may not be necessary to compare the elongated kidney model with any free hand scan images that are smaller than a predetermined size, since it is not possible for such free hand scan images to represent the elongated kidney.

The selected shape model from the data base is displayed to the operator to serve as a guide image during subsequent analysis scanning of the object. Preferably the guide image is displayed as a 3D rendering, including a location label for each of its important features. See a guide image 250 comprising labels 252 in FIG. 4.

Figure 4:
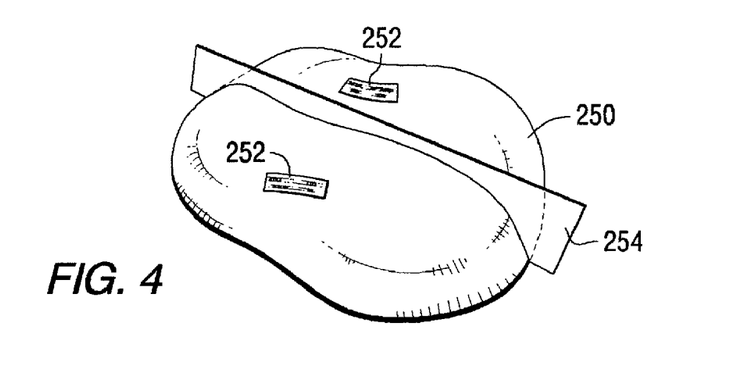
FIG. 4 illustrates a guide image according to the teachings of the present invention.

As the operator rescans the source volume to produce the ultrasound image for analysis, a current scan plane 254 is displayed in the 3D rendered guide image 250, helping the operator to determine the location of the current scan plane relative to the source volume. The labels 252 guide the operator to ensure that important anatomical features of the source volume are insonified. As the operator moves the transducer array to move the scan plane, the scan plane image 254 moves relative to the 3D guide image 250 and different feature labels 252 are displayed responsive to the location of the scan plane on the 3D image. Preferably, the displayed 3D guide image 250 is presented as a smooth semi-transparent model with a relatively low resolution.

To locate the current scan line relative to the 3D guide image and locate the plane on the image, echo responses from the current scan are correlated with the 3D image constructed from the echoes collected during the free hand scan. A correlation peak indicates the location of the current scan on the 3D rendering. If the current scan does not correlate with echoes from the free had scan the current scan plane is not displayed on the guide image.

It is known that non-uniform motion of the transducer probe during the free hand scan (such as a change in the probe velocity) can introduce perturbations in the 3D data set. These perturbations can be compensated during the speckle correlation process to generate an accurate data set from the free hand scan, thereby increasing the likelihood that the correct shape model will be selected.

In an alternative embodiment, the data base of candidate shape models comprises entries that include distorted shape models, i.e., shape models formed by common distortions caused, for example, by the non-uniform motion of the transducer probe during the free hand scan.

In yet another embodiment the data base comprises shape model candidates reflecting various common physiological shapes for the source volume under study. Thus the model selected from the data base can be displayed with only a scale change responsive to the results of the free hand scan. Including different shape models may allow easier and more accurate correlation of the free hand scan model with the candidate shape models in the data base.

Figure 2:
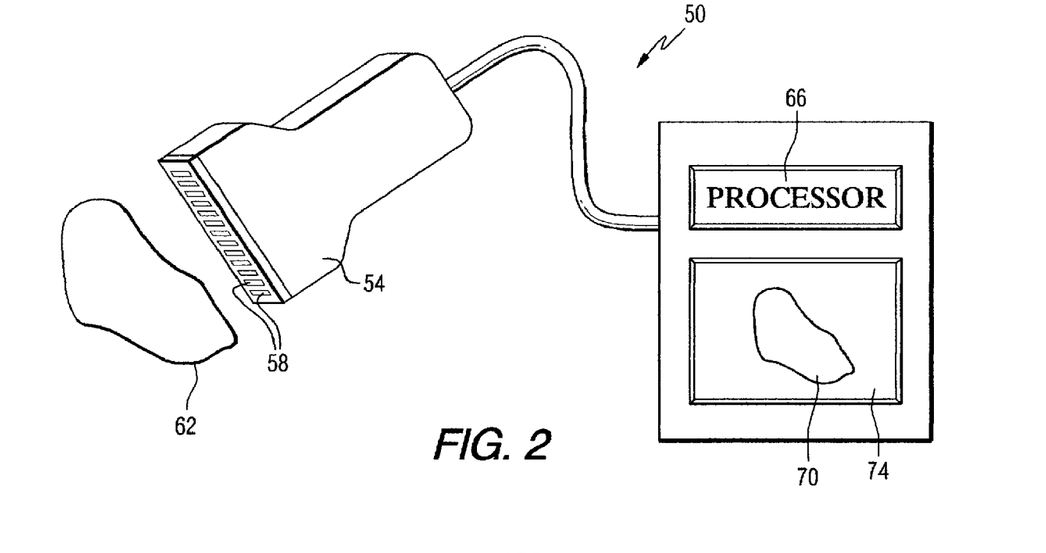
FIG. 2 illustrates an ultrasonic system according to the teachings of the inventions.

FIG. 2 illustrates an ultrasound imaging system 50 to which the teachings of the present invention can be applied. The system 50 includes a probe 54 further including a plurality of ultrasound transducers 58 for transmitting and receiving ultrasound energy during a scan of an object 62. A processor 66 implementing the teachings of one embodiment of the invention processes return echoes received by the transducers 58 to construct an image 70 on a display 74. The processor 66 generates the image based on the return echoes and by selecting a best fit shape model as described above.

Figure 3:
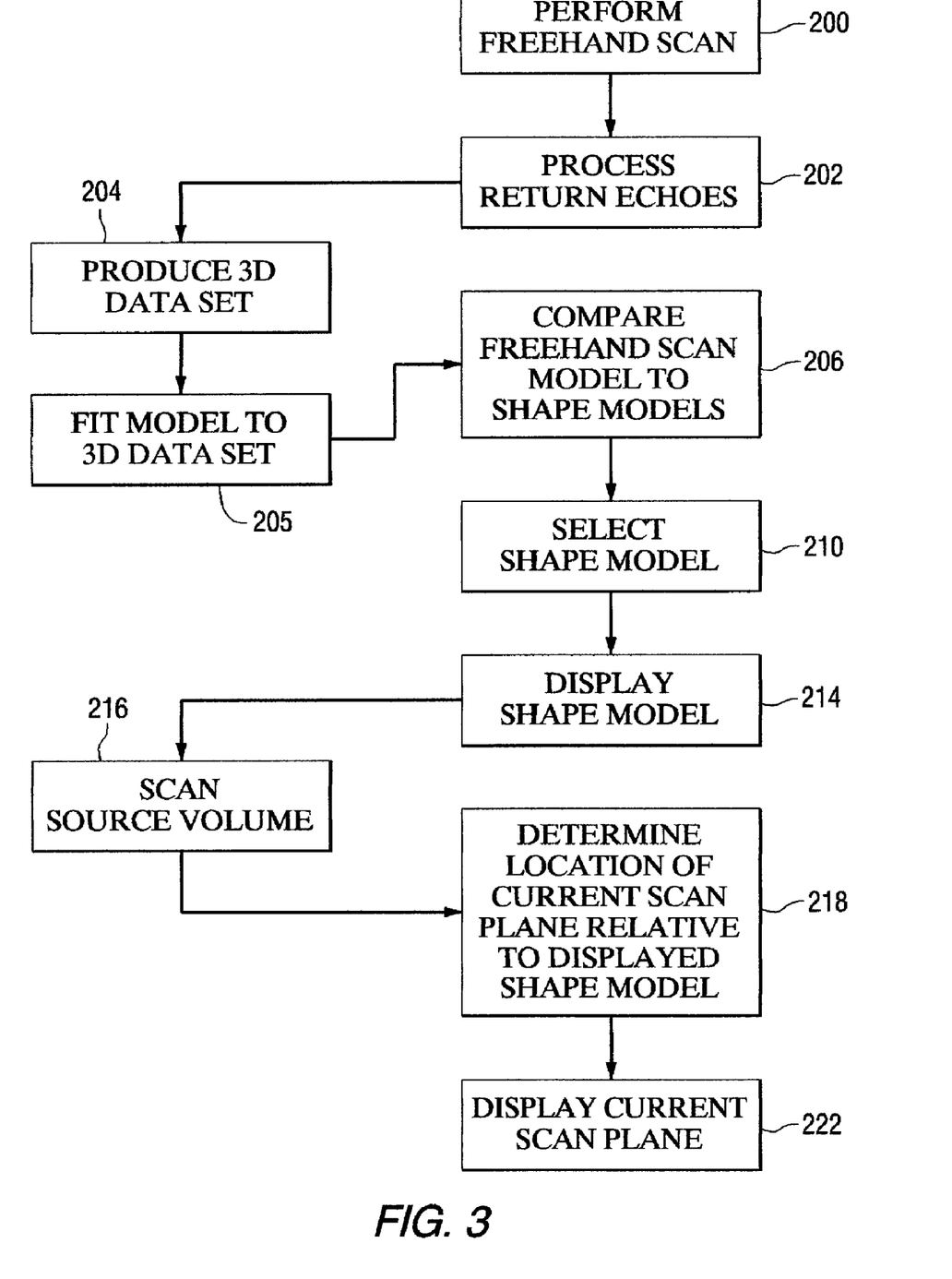
FIG. 3 illustrates a flow chart of processing steps according to one embodiment of the invention.

FIG. 3 illustrates a flow chart illustrating steps associated with one embodiment of the invention. At a step 200, the source volume and surrounding regions are scanned free hand by the operator. The return echoes are processed at a step 202 and the resulting data set produces a 3D data set at a step 204. At a step 205 a free hand scan model is derived from the 3D data set and compared with a plurality of candidate shape models at a step 206. At successive steps 210 and 214 the candidate shape model having the highest correlation with the data set is selected and displayed, preferably as a semi-transparent, relatively low resolution 3D image.

The operator conducts a detailed rescan of the source volume as indicated at a step 216. At a step 218 the current scan plane is determined relative to the displayed shape model and displayed at a step 222 with the shape model display. The return echoes from the detailed rescan are processed to create a typical ultrasound image that is separately displayed from the shape model display.

Persons skilled in the art will recognize that an apparatus, such as a data processing system, including a CPU, memory, I/O, program storage, and other appropriate components, could be programmed or otherwise designed to implement the method embodiments of the invention. Such a system includes appropriate program modules for executing the methods of these embodiments. Moreover, those skilled in the art will appreciate that the invention embodiments may be practiced with other computer system configurations, including hand-held devices, multiprocessor systems, microprocessor-based or programmable consumer electronics, minicomputers, mainframe computers, and the like. The embodiments may also be practiced in a distributed computing environment.

In another embodiment, an article of manufacture, such as a pre-recorded disk or other similar computer program product for use with the data processing system includes storage media and a program recorded thereon for directing the data processing system to facilitate the practice of the methods of the inventions. Such apparatus and articles of manufacture fall within the spirit and scope of the inventions.

The inventions have been described in the general context of computer-executable instructions, such as program modules, executed by a computer. Generally, program modules include routines, programs, objects, components, data structures, etc. that perform particular tasks or implement particular abstract data types. For example, the software programs that underlie the inventions can be coded in different languages, for use with different processing platforms.

Although the embodiments of the invention have been described with respect to imaging bodily organs, the teachings are applicable to other volumetric objects. While the various embodiments of the invention have been described in what is presently considered to be a preferred embodiment, many variations and modifications will become apparent to those skilled in the art. Accordingly, it is intended that the inventions not be limited to the specific illustrative embodiments but be interpreted within the full spirit and scope of the appended claims.

This written description of the embodiments of the invention uses examples to disclose the inventions, including the best mode, and also to enable any person skilled in the art to make and use the inventions. The patentable scope of the inventions are defined by the claims, and may include other examples that occur to those skilled in the art. Such other examples are intended to be within the scope of the claims if they have structural elements or process steps that do not differ from the literal language of the claims, or if they include equivalent structural elements or process steps with insubstantial differences from the literal language of the claims.

What is claimed is:

1. A method for producing a three-dimensional guide image of an object comprising:
   insonifying the object with a free hand scan of the object using an external ultrasound probe;
   receiving, at the probe, first return echoes from the object, the first return echoes representing cross-sectional planes through the object; processing the first return echoes to generate a 3D data set comprising a 3D representation of representing the object;
   comparing the 3D data set with a plurality of differently shaped 3D candidate models of the object; selecting a best fit 3D model from among the candidate 3D models responsive to the step of comparing, the best fit model serving as the 3D guide image; and
   superimposing a current 2D ultrasound scan plane over the best fit model serving as the 3D guide image, the guide image for use by an operator as the current 2D scan plane is generated to control the ultrasound probe to ensure desired regions of the object are insonified during the 2D ultrasound scan.

2. The method of claim 1 wherein the step of I insonifying the object further comprises compensating for perturbations induced by non-uniform motion of the external ultrasound probe during the free hand scan.

3. The method of claim 1 wherein the step of comparing further comprises correlating the 3D data set of the free hand scan model with the plurality of differently shaped 3D candidate models and the step of selecting further comprises determining one of the plurality of differently shaped 3D candidate models with the highest correlation.

4. The method of claim 1 further comprising:
insonifying regions of the object during the 2D current ultrasound scan; receiving second return echoes from the regions of the object; and displaying a current scan plane responsive to the second return echoes on the guide image, wherein the guide image comprises a three dimensional image and the current scan plane comprises a plane intersecting the guide image.

5. The method of claim 4 wherein the step of superimposing further comprises correlating the second return echoes from the regions of the object and the guide image to determine a location of the current scan plane relative to the guide image.

6. The method of claim 1 wherein the step of superimposing further comprises displaying the guide image at a first resolution and displaying the image of the current scan plane at a second resolution greater than the first resolution.

7. The method of claim 1 wherein the step of processing the first return echoes further comprises correlating the first return echoes from a plurality of substantially parallel scan planes.

8. The method of claim 1 wherein the plurality of differently shaped 3D candidate models comprise static shape models of different physiological shapes for one or more objects.

9. The method of claim 1 wherein the plurality of differently shaped 3D candidate models comprise static shape models of different scales for one or more objects.

10. The method of claim 1 wherein the step of comparing further comprises generating a potential field responsive to the 3D data set, applying the potential field to a model surface to conform the model surface to the potential field and comparing the model surface to the plurality of differently shaped 3D candidate models.

11. The method of claim 10 wherein the step of applying the potential field to the model surface further comprises filtering the 3D data set.

12. The method of claim 1 wherein the step of superimposing further comprises displaying the guide image with labels identifying features thereof.

13. An ultrasonic imaging apparatus for producing a three-dimensional guide image of an object, the apparatus comprising: a plurality of ultrasonic transducers for generating ultrasonic energy during a free hand first scan, for receiving first echoes from the object, the first echoes representing cross-sectional planes through the object; a processor for generating a 3D data set according to the first echoes, the 3D data set representing the object, the processor for selecting a best fit shape model from among a plurality of differently shaped 3D candidate models of the object, the step of selecting responsive to the 3D data set; and a display for superimposing a current 2D ultrasound scan plane over the best fit model serving as the 3D guide image, the guide image for use by an operator as the current 2D scan plane is generated to control the ultrasound probe to ensure desired regions of the object are insonified during the 2D ultrasound scan.

14. The ultrasonic imaging apparatus of claim 13 wherein the plurality of ultrasonic transducers comprise a one dimensional array of transducers or a two-dimensional array of transducers.

15. The ultrasonic imaging apparatus of claim 13, wherein the best fit shape model comprises a deformable model defined by mass elements and connectors between mass elements.

16. The ultrasonic imaging apparatus of claim 13, wherein responsive to the 3D data set the processor generates a free hand scan model for correlating with the plurality of differently shaped 3D candidate models to select the best fit shape model.

17. The ultrasonic imaging apparatus of claim 13 wherein during a second scan the plurality of ultrasonic transducers receive second echoes from 2D scan planes of the object, the 2D scan planes superimposed over the best fit model serving as the 3D guide image.

18. The ultrasonic imaging apparatus of claim 17 wherein the display depicts a three-dimensional guide image and a two-dimensional indication of the location of the current scan plane responsive to the second echoes.

19. The ultrasonic imaging apparatus of claim 13 wherein the plurality of shape models comprise at least one of static shape models of different physiological shapes for one or more objects and static shape models of different scales for one or more objects.

20. The ultrasonic imaging apparatus of claim 13, wherein the 3D guide image further comprises labels identifying features of the guide image.

21. A computer software code for producing a three-dimensional guide image of an object responsive to insonifying the object during a first scan, comprising: tangible non-transitory computer readable media, the media further comprising:
a software module for receiving first return echoes from the object responsive to insonifying the object during a free hand first scan of the object using an external ultrasound probe, wherein the first return echoes represent cross-sectional planes through the object;
a software module for processing the first return echoes to generate a 3D data set comprising a 3D representation of representing the object;
a software module for comparing the data set with a plurality of differently shaped 3D candidate models of the object;
a software module for selecting a best fit 3D model from among the candidate 3D models responsive to the software module for comparing, the best fit model serving as the 3D guide image; and
a software module for superimposing a current 2D ultrasound scan plane over the best fit model serving as the 3D guide image, the guide image for use by an operator as the current 2D scan plane is generated to control the ultrasound probe to ensure desired regions of the object are insonified during the 2D ultrasound scan.

22. The computer software code of claim 21 further comprising a software module for compensating perturbations induced by non-uniform motion of the external ultrasound probe during the free hand first scan of the object.

23. The computer software code of claim 21 wherein the software module for comparing the free hand scan model with the plurality of differently shaped 3D candidate models further comprises correlating the free hand scan model with the plurality of differently shaped 3D candidate models of the object and the software module for selecting further comprises determining one of the plurality of differently shaped 3D candidate models with the highest correlation.

24. The computer software code of claim 21 wherein the software module for processing the first return echoes correlates the first return echoes from a plurality of substantially parallel scan planes.

25. The computer software code of claim 21 further comprising a computer software code database storing the plurality of differently shaped 3D candidate models, wherein the plurality of differently shaped 3D candidate models comprise static shape models of different physiological shapes for one or more objects and static shape models of different scales for one or more objects.

26. The computer software code of claim 21 wherein the software module for comparing further generates a potential field responsive to the 3D data set, applies the potential field to a model surface to conform the model surface to the potential field and compares the model surface to the plurality of differently shaped 3D candidate models.

27. The computer software code of claim 26 wherein the software module for applying the potential field to the model surface further comprises filtering the data set.

28. The computer software code of claim 21 wherein the software module for superimposing further comprises displaying guide image labels identifying features of the guide image.

* * * * *

UNITED STATES PATENT AND TRADEMARK OFFICE
CERTIFICATE OF CORRECTION

PATENT NO. : 7,925,068 B2  
APPLICATION NO. : 11/670286  
DATED : April 12, 2011  
INVENTOR(S) : Hoctor et al.

Page 1 of 1

It is certified that error appears in the above-identified patent and that said Letters Patent is hereby corrected as shown below:

On the Title page item (54) and in Column 1, Line 5, in Heading, delete "INVENTIONS", and insert -- INVENTION --, therefor.

On the Title Page, in item (56), under "OTHER PUBLICATIONS", in Column 2, Line 1, delete "Potetial" and insert -- Potential --, therefor.

On Page 2, in item (56), under "OTHER PUBLICATIONS", in Column 2, Line 2, delete "physiclogical" and insert -- physiological --, therefor.

On Page 2, in item (56), under "OTHER PUBLICATIONS", in Column 2, Line 11, delete "Piezoeletric" and insert -- Piezoelectric --, therefor.

In Column 1, Line 12, in Heading, delete "INVENTIONS", and insert -- INVENTION --, therefor.

In Column 4, Line 12, in Heading, delete "INVENTIONS", and insert -- INVENTION --, therefor.

In Column 8, Line 58, in Claim 2, delete "I" before "insonifying".

Signed and Sealed this  
Twenty-sixth Day of July, 2011

David J. Kappos  
*Director of the United States Patent and Trademark Office*